United States Patent [19]

Brewster

[11] Patent Number: 6,086,860
[45] Date of Patent: Jul. 11, 2000

[54] ALCOHOLIC ANTIPERSPIRANT AEROSOL SPRAY PRODUCTS

[75] Inventor: David Allen Brewster, Shelton, Conn.

[73] Assignee: Chesebrough-Pond's USA Co., divsion of Conopco, Inc., Greenwich, Conn.

[21] Appl. No.: 09/286,971

[22] Filed: Apr. 6, 1999

Related U.S. Application Data

[62] Division of application No. 08/944,456, Oct. 6, 1997, Pat. No. 5,911,977.

[51] Int. Cl.$^7$ .............................. A61K 7/32; A61K 7/38; A61K 7/00
[52] U.S. Cl. .............................. 424/65; 424/68; 424/400; 424/401
[58] Field of Search .................... 424/65, 66, 67, 424/68, 400, 401

[56] References Cited

U.S. PATENT DOCUMENTS

| | | | |
|---|---|---|---|
| 3,792,068 | 2/1974 | Luedders et al. | 424/65 |
| 3,974,270 | 8/1976 | Kenkare et al. | 424/65 |
| 4,695,451 | 9/1987 | Straw et al. | 424/65 |

FOREIGN PATENT DOCUMENTS

| | | |
|---|---|---|
| 0 275 695 | 12/1987 | European Pat. Off. . |
| 2 274 278 | 6/1975 | France . |
| 2 048 229 | 4/1980 | United Kingdom . |
| 96/18378 | 6/1996 | WIPO . |

*Primary Examiner*—Shelley A. Dodson
*Attorney, Agent, or Firm*—Milton L. Honig

[57] ABSTRACT

An antiperspirant aerosol spray product is provided packaged in a metal can. Within the can is an antiperspirant aerosol spray composition that includes a propellant, a $C_1$–$C_3$ alcohol and an antiperspirant aluminum astringent salt having a water loss under drying no greater than about 8%. Corrosion and malodor can be minimized by use of low water containing antiperspirant astringent salts even in the presence of very substantial amounts of alcohol which normally tends to accelerate the corrosion process.

7 Claims, No Drawings

ALCOHOLIC ANTIPERSPIRANT AEROSOL SPRAY PRODUCTS

This is a Divisional of Ser. No. 08/944,456 filed Oct. 6, 1997 now U.S. Pat. No. 5,911,977.

BACKGROUND OF THE INVENTION

1. Field of the Invention

The invention concerns antiperspirant aerosol spray products with high levels of alcohol dispensed from pressurized metal cans.

2. The Related Art

Aerosol spray cans are widely used as delivery systems for deodorants and antiperspirants. Corrosion is not a problem for aerosol dispensers formed of glass, aluminum, plastic or even certain types of treated steel. Unfortunately, these materials are not as economical as lower grade or even tin-plated steel. These cans are subject to rust and loss of propellant. Moreover, oxidation can transform formulation components such as those constituting the fragrance. Odor is thereby adversely affected.

Use of alcohol in antiperspirant spray formulations is highly desirable for several reasons. Alcohol provides for good suspension of the antiperspirant active salts. An improved fragrance lift can also be achieved through the use of alcohol. Unfortunately, high levels of alcohol accelerate detinning, pitting and other forms of corrosion. For this reason, commercial products generally are not formulated with alcohol in amounts higher than 10%.

Accordingly, it is an object of the present invention to provide an antiperspirant aerosol spray product which permits high levels of alcohol to be formulated without fear of metal corrosion.

Another object of the present invention is to provide an antiperspirant aerosol spray product with sufficiently high levels of alcohol to improve the fragrance lift.

Still another object of the present invention is to provide an antiperspirant aerosol spray product which is faster drying than previous formulations.

These and other objects of the present invention will become more readily apparent through consideration of the following summary and detailed description.

SUMMARY OF THE INVENTION

An antiperspirant aerosol spray product is provided which includes:
(A) a pressurized metal can fitted with an aerosol sprayhead; and
(B) an antiperspirant composition held within the metal can including:
  (i) from 1 to 40% by weight of an aluminum astringent salt having a water loss no greater than 8% by weight of the salt;
  (ii) a volatile compound selected from the group consisting of from 10 to 70% by weight of a $C_1$–$C_3$ alcohol and from 10 to 80% by weight of a propellant.

DETAILED DESCRIPTION OF THE INVENTION

Now it has been found that corrosion of metal cans can be significantly inhibited even in the presence of relatively large amounts of alcohol. The discovery is based upon the use of only aluminum astringent salts having a water loss no greater than 8% as measured by USP Physical Tests Water Determination Gravimetric Method 921 III, with the modification that a 2 gram sample of aluminum astringent salt is dried for 3 hours at 105° C.

Subject to the water loss requirement, suitable astringent salts for the present invention may be inorganic or organic salts of aluminum, zirconium, zinc and mixtures thereof. Salts useful as astringents or as components of astringent aluminum complexes include aluminum halides, aluminum hydroxyhalides, zirconyl oxyhalides, zirconyl hydroxyhalides and mixtures of these salt materials.

Aluminum salts of this type include aluminum chloride and the aluminum hydroxyhalides having the general formula $Al_2(OH)_xQ_y \cdot XH_2O$ where Q is chlorine, bromine or iodine, where x is 2 to 5 and x+y=6 and x and y do not need to be integers, and where X is about 1 to 6.

Several types of complexes utilizing the above astringent salts are known in the art. For example, U.S. Pat. No. 3,792,068 (Luedders et al.), discloses complexes of aluminum, zirconium and amino acids such as glycine. Complexes reported therein and similar structures are commonly known as ZAG. The ZAG complexes ordinarily have an Al:Zr ratio of from about 1.67 to 12.5 and a Metal:Cl ratio of from about 0.73 to 1.93. The preferred amino acid for preparing such ZAG-type complexes is glycine of the formula $CH_2(NH_2)COOH$. Spherical ZAG, with particle size 1 to 100 microns, is especially preferred.

More specifically, the following is a list of antiperspirant actives which may be useful for the present invention and which have approved listings under the United States Food & Drug Administration, Federal Register. They include aluminum chloride, aluminum chlorohydrate, aluminum chlorohydrex, aluminum chlorohydrex PEG, aluminum chlorohydrex PG, aluminum dichlorohydrate, aluminum dichlorohydrex PEG, aluminum dichlorohydrex PG, aluminum sesquichlorohydrate, aluminum sesquichlorohydrex PEG, aluminum sesquichlorohydrex PG, aluminum sulfate, aluminum zirconium octachlorohydrate, aluminum zirconium octachlorohydrex GLY, aluminum zirconium pentachlorohydrate, aluminum zirconium pentachlorohydrex GLY, aluminum zirconium tetrachlorohydrate, aluminum zirconium trichlorohydrate, aluminum zirconium tetrachlorohydrate GLY, and aluminum zirconium trichlorohydrate GLY.

Most preferred is aluminum chlorohydrate (ACH A426) available from Summit Research Laboratories, Huguenot, N.Y.

Amounts of the active aluminum astringent salt may range from 1 to 40%, preferably from 5 to 30%, optimally from 8 to 15% by weight of the composition.

A second essential element of compositions according to the present invention is that of a $C_1$–$C_3$ alcohol. Most preferred is ethanol, especially SD Alcohol 40. However, it is possible also to use methanol or isopropanol. Amounts of the alcohol may range from 10 to 70%, preferably from 12 to 40%, optimally from 15 to 30% by weight of the composition.

Propellants are a further essential element of compositions according to the present invention. Typical propellants are volatile organic compounds of boiling point less than 40° C., preferably less than 20° C. and optimally no higher than 10° C. Suitable propellant classes include $C_1$–$C_6$ hydrocarbons, $C_2$–$C_8$ dialkyl ethers, carbon dioxide and halo hydrocarbons. Among the useful hydrocarbons are propane, isopropane, butane, isobutane, isopentane, pentane and mixtures thereof. Propellants are available under the mark A31

(purely isobutane) and A45 isobutane/isopropane) from the Phillips Petroleum Company. Most preferred is propellant A50 which is a blend of isobutane/propane. Another useful propellant is dimethyl ether.

A number of optional components may also be part of compositions according to the present invention. These include bulking agents, volatile silicones, nonvolatile emollients and minor ingredients.

Bulking or suspending agents when present may be found at levels of from 1 to 50%, preferably from 2 to 8%.

Clays and colloidal pyrogenic silica are the preferred materials for use as bulking/suspending agents. Colloidal silica is available commercially as Cab-O-SIl®, a submicroscopic particulate pyrogenic silica.

Clay bulking/suspending agents suitable for use in the compositions of the present invention are selected from the group consisting of montmorillonite clays and hydrophobically treated montmorillonite clays. Examples of these clays include the bentonites, hectorites, and colloidal magnesium aluminum silicates. The latter are complexes of colloidal magnesium aluminum silicate richer in magnesium than aluminum. Commercially they are available as Veegum (R.T. Vanderbilt Co.). Preferred hydrophobically treated montmorillonite clays are available under the trademark of "Bentone". These are prepared by reacting bentonite in a cation exchange system with an amine. Different amines are reacted to obtain a variety of Bentones, which may also differ in proportions of $SiO_2$, MgO and $Al_2O_4$. Specific examples of Bentones within the scope of the present invention are Bentone 38, Bentone 34, Bentone 27, Bentone 14, and Bentone LT, all of which have a particle size of below about 5 microns and are commercially available from Rheox, Inc.

Volatile silicones may be incorporated into compositions of the present invention. They can either be cyclic or linear polydimethylsiloxanes. Amounts of this material may range from 10 to 80%, preferably from 15 to 70% by weight. Commercially they are available from Dow Corning Corporation as DC 344, 345, 244, 246 and 245.

Non-volatile emollients are further useful components. These may be selected from non-volatile silicones, liquid paraffins (such as mineral oil) and esters. illustrative of the silicones are polyalkyl siloxane, polyalkylaryl siloxane or polyether siloxane copolymer (e.g. dimethiconol). Commercially they are available from Dow Corning as, for instance, DC 556 or DC 200 series. Illustrative ester emollients are those formed from $C_1$–$C_{20}$ alkanols esterified with $C_8$–$C_{22}$ alkanoic acids. Examples include isopropyl myristate, lauryl myristate, isopropyl palmitate, diisopropyl sebacate and diisopropyl adipate. Most preferred is isopropyl palmitate. Amounts of the emollient may range from 0.5 to 30%, preferably from 5 to 20%, optimally from 8 to 15% by weight.

Powdered fillers other than bulking agents may also be incorporated. Particularly preferred is talc, sodium bicarbonate, corn starch and modified starches. Most preferred is talc. Amounts of the powdered filler may range from 0.5 to 15%, preferably from 1 to 10%, optimally from 1.5 to 5% by weight.

Adjunct minor ingredients can be present including fragrance and anti-clogging agents for keeping the spray nozzle free of solid occlusions.

Pressurized aerosol cans according to the present invention are available from the U.S. Can Company and from the Crown, Cork and Seal Company. Most preferred are 0.25 pound tin-plated steel cans.

The following examples will more fully illustrate the embodiments of this invention. All parts, percentages and proportions referred to herein and in the appended claims are by weight of the composition unless otherwise indicated.

EXAMPLE 1

A series of experiments were conducted to evaluate the effect of aluminum chlorohydrate salts with different degrees of complexed water. Sample formulations which were tested are outlined under Table I.

TABLE I

| | SAMPLE (WEIGHT %) | | | |
|---|---|---|---|---|
| INGREDIENTS | A | B | C | D |
| DC 344 ® | 25.10 | 15.10 | 25.10 | 15.10 |
| Isopropylpalmitate | 10.50 | 10.50 | 10.50 | 10.50 |
| Bentone 38CG ® | 1.50 | 1.50 | 1.50 | 1.50 |
| SD Alcohol (200 PF) | 10.00 | 20.00 | 10.00 | 20.00 |
| Fragrance | 0.70 | 0.70 | 0.70 | 0.70 |
| Talc | 3.00 | 3./00 | 3.00 | 3.00 |
| ACH A425 (17.5% moisture) | 9.20 | 9.20 | — | — |
| ACH A426 (7.4% moisture) | — | — | 9.20 | 9.20 |
| A50 Propellant | 40.00 | 40.00 | 40.00 | 40.00 |
| Stability Results | | | | |
| Odor (remaining in can) | strong malodor | strong malodor | mild odor characteristic of original fragrance | mild odor characteristic of original fragrance |
| Corrosion | severe corrosion pitting | severe corrosion pitting | minor corrosion no pitting | minor corrosion no pitting |

Samples A through D were prepared in the following manner. DC 344®, isopropylpalmitate and Bentone 38CG® were mixed together for 30 minutes. Thereafter, the SD alcohol and fragrance were blended into the reactor. After a further period of stirring, talc and aluminum chlorhydrate (ACH) were added to the mixture. Product was then homogenized through a Manton Gaulin Homogenizer. The resultant formulation was then filled into tin plated aerosol containers and A50 propellant was charged under pressure into the cans. These cans were size 202×509 from U.S. Can Company, ¼ pound tin-plated with IL-30 lining (clear lacquer).

A series of four cans were prepared for each sample. These were then maintained at 120° F. for a period of four months. Every month, one can from each of the formulas was opened to analyze for pitting and corrosion. The results after four months are reported at the bottom of Table I. Less corrosion was seen in Samples C and D incorporating the A426 type of aluminum chlorohydrate. A426 includes only 7.4% water adsorbed with the aluminum salt. By contrast, malodor and pitting were very significant problems with Samples A and B containing A425. This aluminum salt contains 17.5% adsorbent water as determined by the loss on drying tests. From these experiments it is to be concluded that even in the presence of relatively high amounts of alcohol (20%), corrosion is inhibited through use of aluminum salts with less than about 8% adsorbed water.

EXAMPLES 2–8

Other aerosol formulations suitable for the present invention are outlined in Table II.

TABLE II

| INGREDIENTS | \multicolumn{7}{c}{EXAMPLE (WEIGHT %)} |
|---|---|---|---|---|---|---|---|

| INGREDIENTS | 2 | 3 | 4 | 5 | 6 | 7 | 8 |
|---|---|---|---|---|---|---|---|
| DC 344 | 10.10 | 10.10 | 10.10 | 15.10 | 15.10 | 15.10 | 20.60 |
| Isopropylpalmitate | 10.50 | 5.50 | 0.50 | 10.50 | 10.50 | 10.50 | — |
| Bentone 38CG | 1.50 | 1.50 | 0.50 | 3.50 | 3.50 | 1.50 | 1.50 |
| SD Alcohol (200 PF) | 25.00 | 10.00 | 10.00 | 10.00 | 20.00 | 20.00 | 25.00 |
| Fragrance | 0.70 | 0.70 | 0.70 | 0.70 | 0.70 | 0.70 | 0.70 |
| Talc | 3.00 | 3.00 | 1.00 | 1.00 | 1.00 | 3.00 | 3.00 |
| ACH A426 | 9.20 | 9.20 | 7.20 | 19.20 | 9.20 | 9.20 | 9.20 |
| A50 | 40.00 | 60.00 | 70.00 | 40.00 | 40.00 | 40.00 | 40.00 |

The foregoing description and examples illustrate selected embodiments of the present invention. In light thereof variations and modifications will be suggested to one skilled in the art, all of which are within the spirit and purview of this invention.

What is claimed is:

1. An antiperspirant aerosol spray product comprising:
   (A) a pressurized metal can fitted with an aerosol sprayhead; and
   (B) an antiperspirant composition held within the metal can comprising:
   (i) from 1 to 40% by weight of an aluminum astringent salt having a water loss no greater than 8% by weight of the salt;
   (ii) a volatile compound selected from the group consisting of from 10 to 70% by weight of a $C_1$–$C_3$ alcohol and from 10 to 80% by weight of a propellant.

2. The product according to claim 1 wherein the propellant is a hydrocarbon.

3. The product according to claim 1 wherein the alcohol is ethanol.

4. The product according to claim 1 wherein the alcohol is present from 12 to 40% by weight.

5. The product according to claim 1 wherein the composition further comprises from 0.5 to 30% by weight of an ester emollient formed from esterification of a $C_1$–$C_{20}$ alkanol with a $C_8$–$C_{22}$ alkanoic acid.

6. The product according to claim 1 wherein the composition further comprises from 1 to 50% by weight of a bulking agent.

7. The product according to claim 6 wherein the bulking agent is a hydrophobically treated bentonite.

* * * * *